United States Patent [19]

Starr et al.

[11] Patent Number: 5,441,046
[45] Date of Patent: Aug. 15, 1995

[54] QUICK RELEASE MECHANISM FOR NASAL AND/OR ORAL GAS DELIVERY MASK

[75] Inventors: John R. Starr, Leechburg; Eric W. Starr, Pittsburgh; Mary T. Walthour, Pitcairn, all of Pa.

[73] Assignee: Respironics, Inc., Murrysville, Pa.

[21] Appl. No.: 128,902

[22] Filed: Sep. 29, 1993

[51] Int. Cl.6 .............................................. A62B 18/08
[52] U.S. Cl. ............................ 128/207.11; 128/206.27
[58] Field of Search ..................... 128/205.25, 206.21, 128/206.24, 206.27, 206.28, 207.11, 207.13, 206.12, 201.24, 202.27, 203.29, 206.26; 2/6.2, 6.5, 421, 425, 422, 10, 9

[56] References Cited

U.S. PATENT DOCUMENTS

| | | | |
|---|---|---|---|
| 2,212,862 | 8/1940 | Hirsch | 24/198 |
| 2,290,885 | 7/1942 | Lehmberg | 128/206.15 |
| 2,382,592 | 8/1945 | Whipple | 128/206.12 |
| 2,710,486 | 6/1955 | Blatt | 2/306 |
| 2,867,812 | 1/1959 | Roth et al. | 2/6.2 |
| 2,931,356 | 4/1960 | Schwarz | 128/206.24 |
| 2,970,593 | 2/1961 | Seeler | 2/6.2 |
| 3,056,402 | 10/1962 | Dickinson | 128/206.27 |
| 3,185,148 | 5/1965 | Gaylord | 128/202.27 |
| 3,310,811 | 3/1967 | Jacono, Jr. | 128/201.24 |
| 3,330,273 | 7/1967 | Bennet | 128/146.7 |
| 3,383,706 | 5/1968 | Lobelle | 2/6.5 |
| 3,529,329 | 9/1970 | Burleson | 2/240 |
| 3,548,411 | 12/1970 | Barstow et al. | 2/6.5 |
| 4,193,133 | 3/1980 | Laibach et al. | 2/10 |
| 4,764,989 | 8/1988 | Bourgeois | 2/422 |
| 4,907,300 | 3/1990 | Dampney et al. | 2/6.5 |
| 4,907,584 | 3/1990 | McGinnis | 128/206.24 |
| 4,960,121 | 10/1990 | Nelson et al. | 128/206.24 |
| 5,091,997 | 3/1992 | Foehl | 2/425 |

FOREIGN PATENT DOCUMENTS 217129 10/1957 Australia .............. 128/207.11

Primary Examiner—Kimberly L. Asher
Attorney, Agent, or Firm—Reed Smith Shaw & McClay

[57] ABSTRACT

A quick release/connect mechanism used with nasal and/or oral gas delivery masks. The mechanism attaches to the mask and to the head gear, acting as a connection link. While under normal use the connection remains intact. However, when the release cord is pulled, the mechanism is inclined and becomes free from one of the head gear straps and the connection is broken, allowing the mask to fall quickly from the face. Upon reattachment, the still-adjusted strap simply slips back into place on the mechanism to allow continuation of therapy. Reattachment is accomplished without having to readjust the strap for proper fit.

13 Claims, 5 Drawing Sheets

Fig. 8
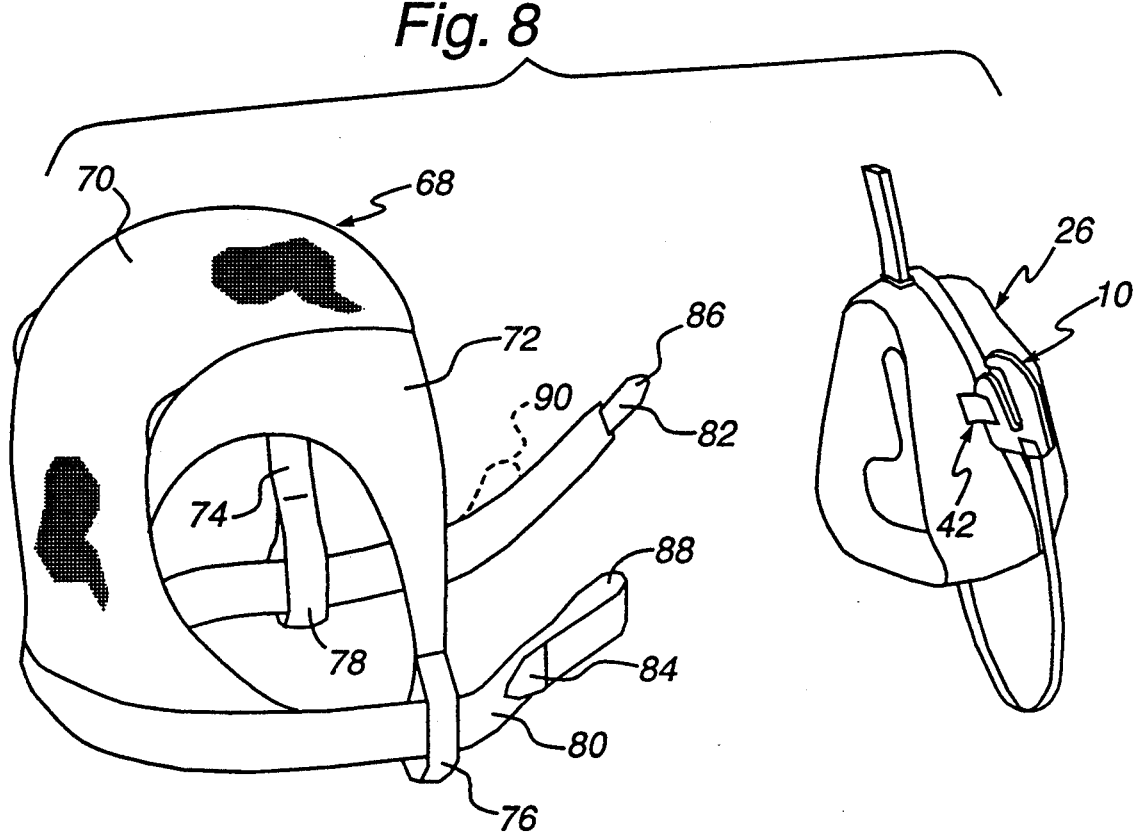
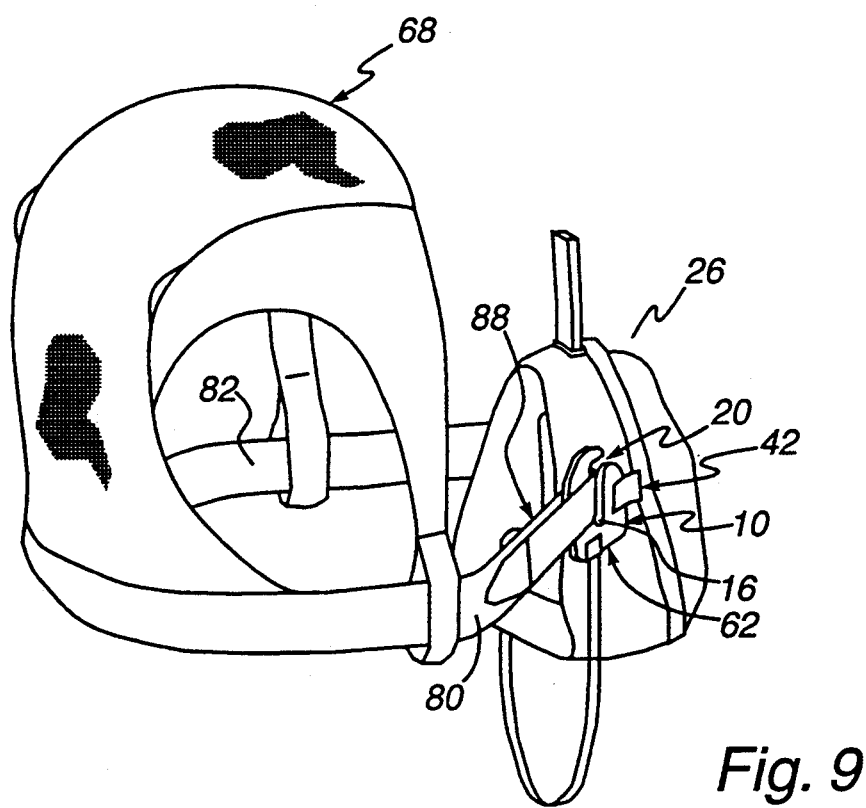
Fig. 9

QUICK RELEASE MECHANISM FOR NASAL AND/OR ORAL GAS DELIVERY MASK

BACKGROUND OF THE INVENTION

1. Field of the Invention

This invention relates to nasal and/or oral gas delivery masks, and more particularly to a quick connect-/release mechanism for such gas delivery masks.

2. Description of Prior Art

Connectors used to connect a harness to a respirator or a mask are known. In one arrangement, each side of the mask is provided with a hook, clip or rivet to which a suitable head band is connected by means of a head band hook. The head band holds the mask on the face of the wearer. See, for example, U.S. Pat. No. 2,290,885 issued to W. H. Lehmberg.

In a second arrangement, an annular spider having radially projecting lugs is mounted at the mask inlet opening. A head harness is provided to hold the mask firmly against the face. The head harness provides upper and lower straps extending above and below the ears. The straps have holes at the ends thereof for receiving the lugs presented by the annular spider. A plurality of the holes is provided on each strap to enable adjustment of the harness for different size heads. See, for example, U.S. Pat. No. 3,330,273 issued to V. R. Bennett.

In either of the above-described arrangements, the respirator or mask can be removed only by stretching the head band or strap to release the same from the clip or lug. The stretching of the head band or strap subjects the patient to added stress which should be avoided. Furthermore, the arrangements do not provide means for rapidly removing the respirator or mask.

Another buckle-type connector is known for connecting the ends of straps. The buckle includes a main body having an arm and a slot in which the strap may be inserted. The arm of the buckle further includes a scroll in the inverted cusp for securing the strap. See, for example. U.S. Pat. No. 2,212,862 issued F. Hirsch. The principle purpose of the Hirsch '862 invention is to permit the buckle to be readily attached and detached from a garment, strap or other wearing apparel.

Other examples of fasteners including a main body having an arm and a slot for receiving the ends of a strap will be found in U.S. Pat. Nos. 2,710,486 issued to P. Blatt and 3,529,329 issued to A. Burleson.

SUMMARY OF THE INVENTION

The principle object of this invention is to provide a release/connection mechanism used with nasal or nasal-/oral gas delivery masks by which the mask may be quickly and easily removed.

Another object of this invention is to provide a release/connection mechanism by which the mask may be reattached to the patient without having to readjust for proper fit.

Accordingly to one aspect of this invention, a patient gas delivery system is provided comprising a mask adapted to fit over the face of a patient and having opposite first an second sides. Head gear, adapted to fit over the head of a patient, provides lower strap means, one extending from each side of the head gear toward the mask. First connector means on the first side of the mask presents a generally vertical, U-shaped slot, having an open top. A first of the lower strap means is received in the U-shape slot through said open top to detachably connect the first of the lower strap means to the first connector means. Pivot means are provided connecting the first connector means to the first side of the mask for resisted pivotal movement of the first connector means from an upright position wherein the first of the lower strap means is connected to the first connector means, to an inclined position wherein the first strap means is quickly disconnected from the first connector means to release the mask. Means also are provided for pivoting the first connector means.

In accordance with another aspect of the present invention, a gas delivery mask is provided comprising a shell adapted to receive conduit means for delivering gas to the mask, and connected thereto a relatively soft cushion having an opening adapted to receive the nose and/or mouth of the patient. The shell and cushion combination presents opposite first and second sides. First connector means is provided having a generally vertical U-shaped slot with an open top. Pivot means connects the first connecting means to the first side of the mask for resisted pivotal movement from a first or upright position wherein the first connector means is positioned for connection to strap means of associated head gear, to a second or inclined position wherein the first connector means hence the U-shaped slot thereof are inclined such that the strap means is quickly disconnected from the first connector means. Means connected to the first connector means are provided for pivoting the first connector means into the second position.

In accordance with still another aspect of the present invention, a quick connect/release tab is provided comprising a main body. An arm on the main body forms an elongated slot therewith. An arcuate end on the arm extends over the elongated slot and cooperates with an end of the main body to provide an entrance opening having a width which is larger than the width of the slot. A first opening is provided in the main body portion adjacent to the entrance opening which is adapted to receive pivot means about which the main body may pivot. A second opening is provided at the bottom end of the arm which is adapted to receive means for pivoting the main body.

These and other objects and advantages of the present invention will become apparent from the following detail description by reference to the accompanying drawings in which:

BRIEF DESCRIPTION OF THE DRAWINGS

FIG. 8 is an exploded isometric view illustrating head gear and the mask of FIG. 2;

FIG. 9 is an isometric view illustrating the head gear attached to the mask of FIG. 8;

DESCRIPTION OF THE PRESENTLY PREFERRED EMBODIMENT(S)

Figure 1:
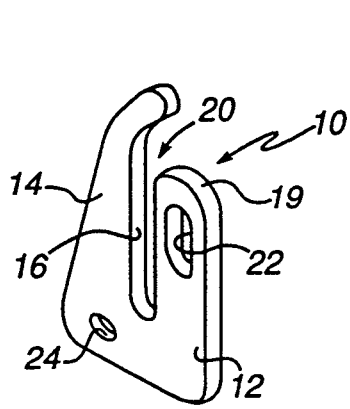
FIG. 1 is an isometric view of first connector means of this invention.

FIG. 1 illustrates a first connector means 10 having a main body portion 12 and an arm 14 forming a slot 16 therewith. The arm 14 presents an arcuate end 18 at its upper end which extends toward the main body 12 and cooperates with an upper end 19 of the main body 12 to define an entrance opening 20 providing access to the slot 16. The entrance opening 20 preferably has a width that is larger than the width of the slot 16 to facilitate entry and exit of strap means associated with a mask, as will be described. The main body 12 presents a first opening 22 adjacent to the entrance opening 20. The main body portion also includes a second opening 24 beneath the arm 14. As will be described, the first opening 22 is adapted to receive a portion of pivot means 42 for pivotally connecting the first connector means 10 to the mask 26; and the second opening 24 is adapted to receive a portion of means for pivoting the first connector means 10.

Figure 2:
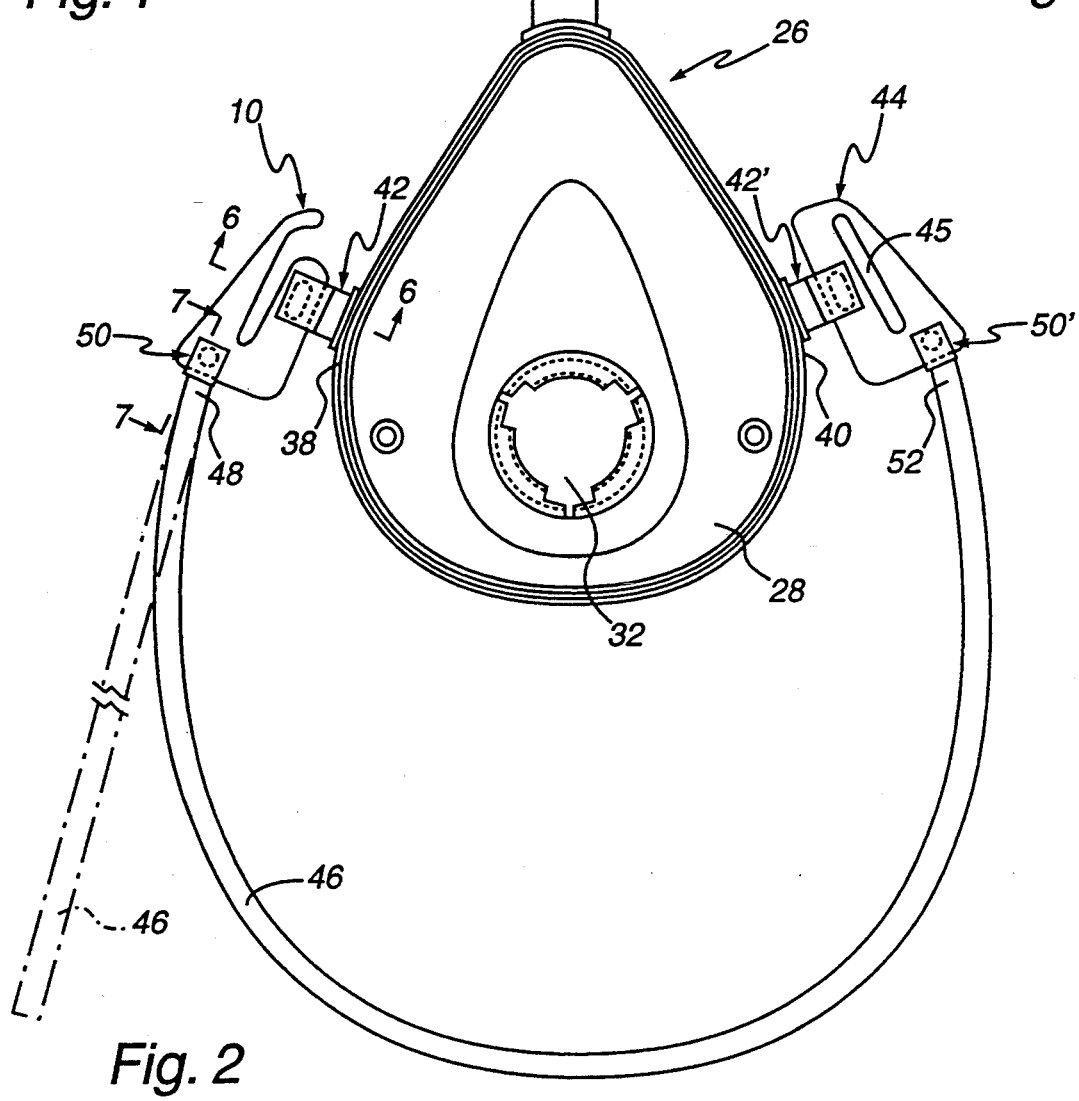
FIG. 2 is a front elevation view of a gas delivery mask incorporating the first connector means of this invention.
Figure 5:
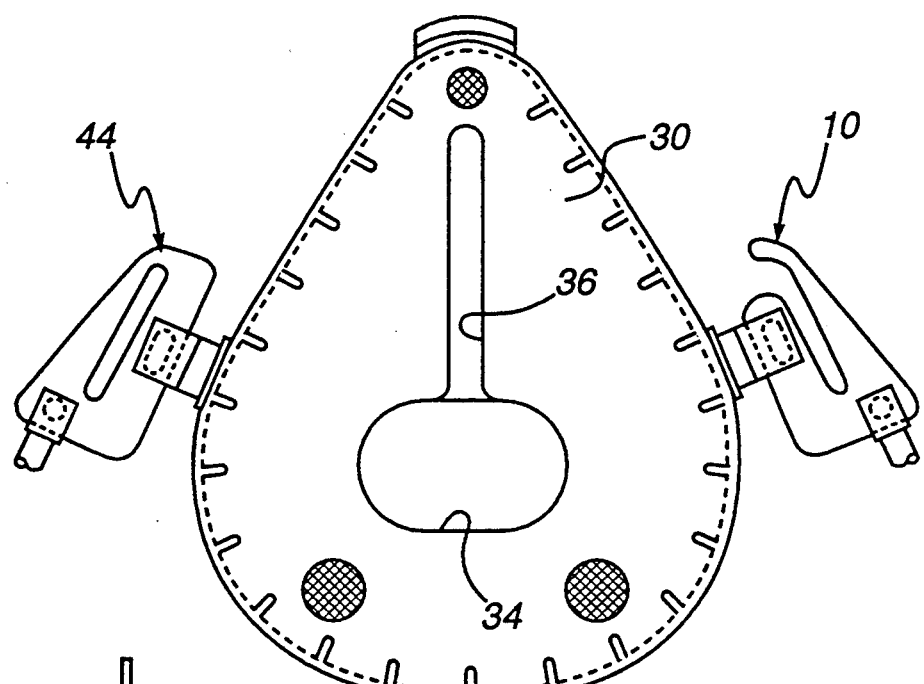
FIG. 5 is a view illustrating the back of the gas delivery mask of FIG. 2.
Figure 4:
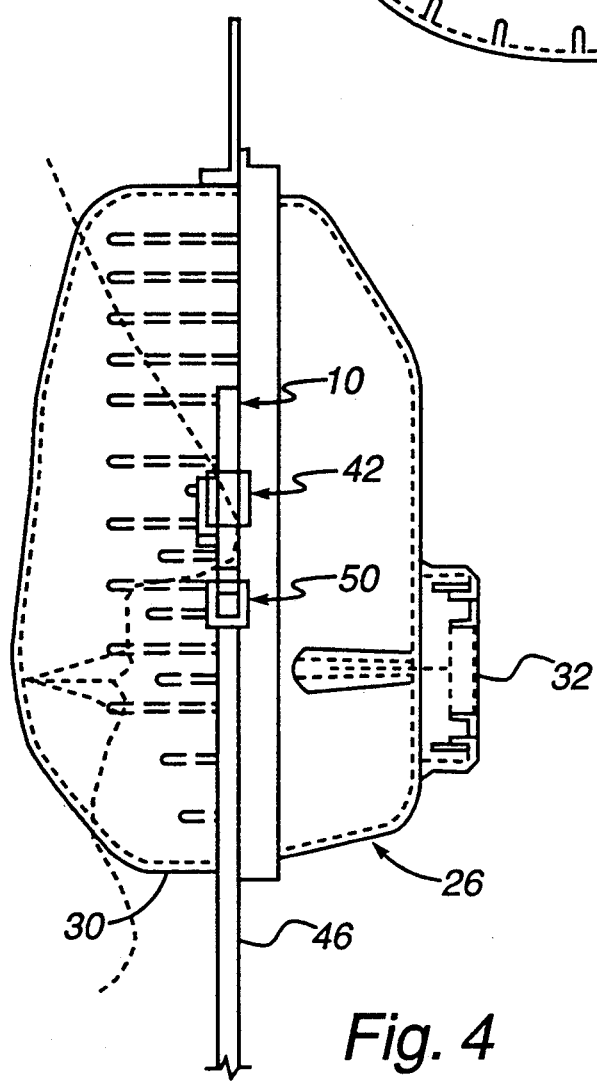
FIG. 4 is a side view of the gas delivery mask of FIG. 1.

Referring to FIGS. 2, 4 and 5, there is illustrated a nasal/oral mask 26 comprising a relatively stiff shell 28 having attached thereto a relatively soft cushion 30. Alternatively, the shell 28 may also be formed from the same relatively soft material as the cushion 30. The shell 28 includes an inlet opening 32 adapted to receive a suitable valve for regulating delivery of gas to the mask 26. As shown in FIG. 4, the cushion 30 is configured to receive the nose and mouth of a patient, which is illustrated in dashed lines. As shown in FIG. 5, the soft cushion 30 presents a mouth opening 34 and a nose opening 36. Alternatively, the mask 26 may, instead, comprise a nasal mask configured to enclose only the nose of a patient or an oral mask configured to enclose only the mouth of a patient.

Returning to FIG. 2, the mask 26 has opposite first and second sides 38, 40. The first connector means 10 is secured to the first side 38 of the mask 26 by pivot means 42. Second connector means 44 is secured to the second side 40 of the mask 26 by pivot means 42'. A cord 46 which, as will be described, facilitates quick removal of the mask 26, has at least one end 48 secured to the first connector means 10 by connection means 50 and depends downwardly therefrom as shown in dash-dot outline. Preferably, the cord 46 has an opposite end 52 which is secured to the second connector means 44 by a connection means 50' thereby forming a loop which is more easily available to be grasped by the patient or the attendant.

Figure 3:
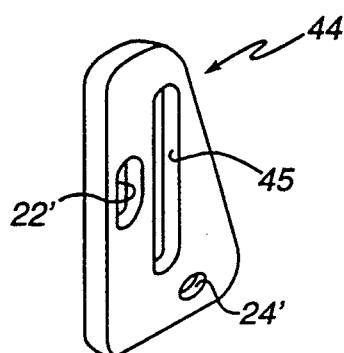
FIG. 3 is an isometric view of second connector means.

Referring to FIG. 3, the second connecting means 44 presents an elongated opening 45 which, as will be described, receives strap means for securing the second side 40 of the mask 26 to the face of a patient. The second connecting means 44 also presents a first opening 22' adjacent to the elongated opening 45, which is used to secure the pivot means 42' to the first connector means 44; and a second opening 24' to which the cord 46 is secured.

The first and second connector means 10, 44 is formed from plastics such as, polycarbonate, ABS and rigid vinyl. The first and second connector means 10, 44 preferably are formed from polycarbonate.

Figure 6:
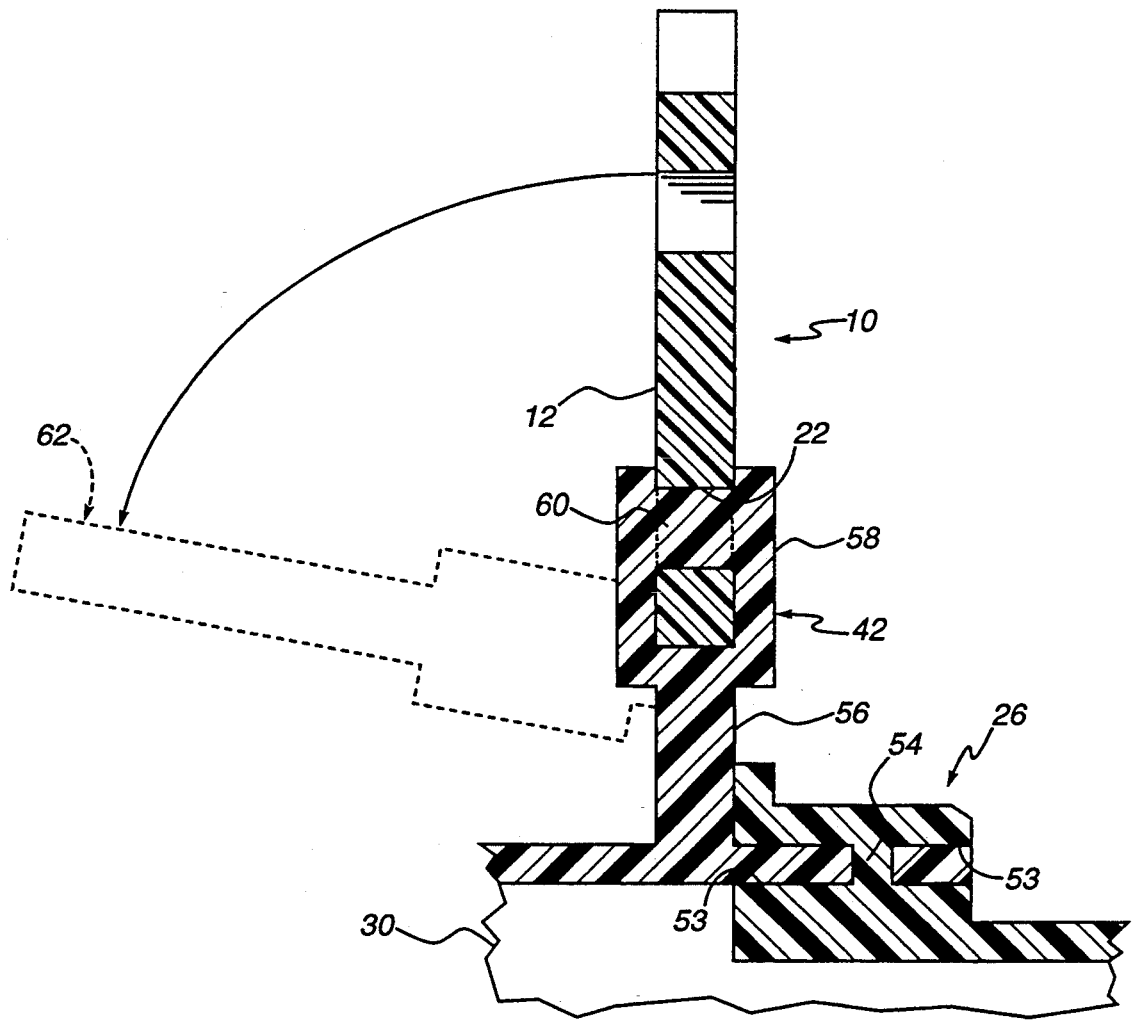
FIG. 6 is a cross-sectional view taken along the line 6—6 of FIG. 2.
Figure 10A:
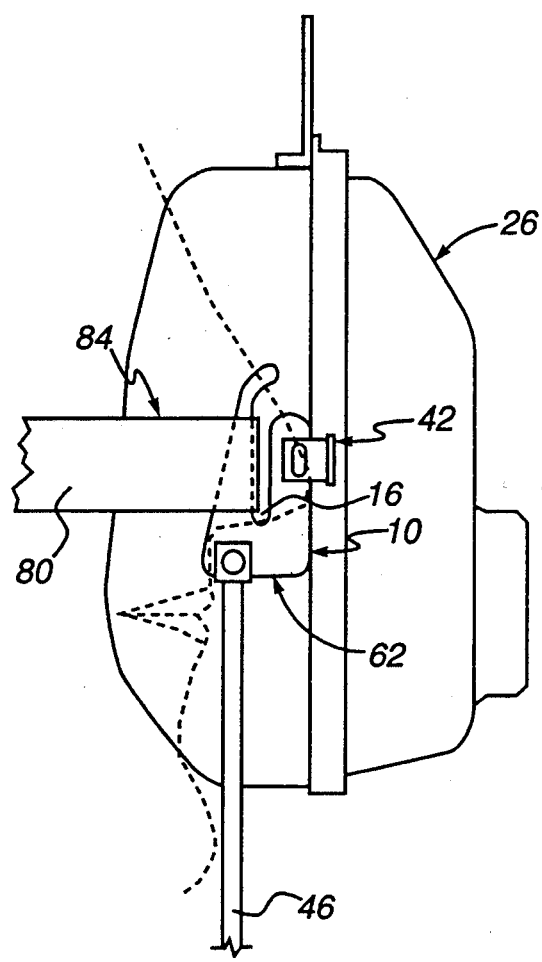
FIG. 10A is a view similar to FIG. 4, illustrating the first connector means in a first or upright position and connected to first strap means.

Referring to FIG. 6, the pivot means 42 preferably formed from resilient material, such as soft vinyl, silicone or rubber, and formed integrally with the soft cushion 30 by a molding process. The pivot means 42 comprises a leg 56 terminating in a bifurcated end 58 which encapsulates a portion of the main body 12 of the first connector means 10, and having a portion 60 filling the first opening 22 of the connector means 10 thereby securing the connector means 10 to the pivot means 42. In a like manner, the material of the soft cushion 30 also flows, during the molding process, into recesses 53 and about posts 54 of the shell 28 thereby securing the cushion 30 to the shell 28. It will be observed in FIG. 6 that the first connector means 10 is pivotal about the leg 56 to a first or upright position 62 illustrated in dashed outlines. The first or upright position 62 of the first connector means 10 is best seen in FIGS. 9 and 10A. As should be evident, the second connector means 44 is pivotal in the same manner about the pivot means 42' to accept strap means 82 of the headgear 68, as will be described.

Figure 7:
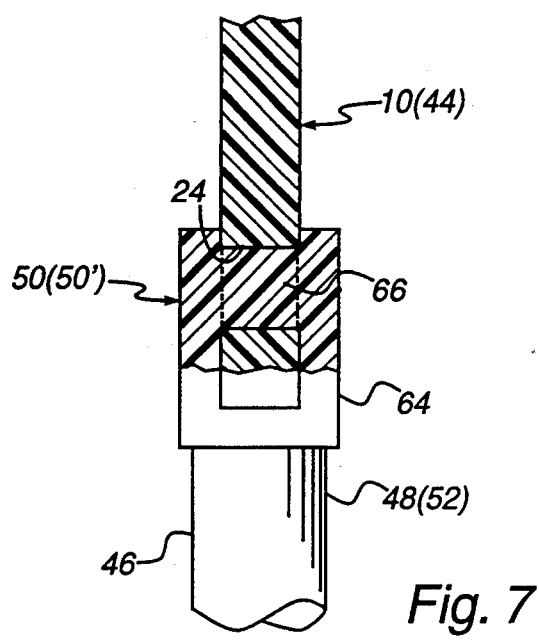
FIG. 7 is a cross-sectional view taken along the line 7—7 of FIG. 2.

Referring to FIG. 7, the connection means 50 (50') by which each cord end 48 (52) of the cord 46 is secured to the connector means 10 (44) preferably are formed from resilient material, such as soft vinyl, silicone or rubber, and formed integrally with the cord 46 by a molding process. The connector means 50, 50' each comprise a bifurcated end 64 encapsulating a lower portion of the connector means 10 (44) and having a portion 66 filling the opening 24 of the connector means 10 (44) thereby securing the bifurcated end 64 to the connector means 10 (44).

In FIG. 8 the mask 26 is shown in juxtaposed relation with head gear 68 of the type described, illustrated and claimed in co-pending application Ser. No. 08/128,984 filed Sep. 28, 1993 and assigned to the assignee of the present invention. It should be noted that the present connector means 10 (FIG. 1) may be used with any headgear incorporating lower strap means such as illustrated at 80, 82 in FIGS. 8 and 9.

For a complete description of the headgear 68, reference is directed to the aforesaid patent application Ser. No. 08/128,984, which application is incorporated herein by reference. However, for the purpose of this invention, it is believed sufficient to state that the head gear 68 comprises a head piece 70 having depending strap means 72, 74 depending from opposite sides thereof and which terminate in depending strap loops 76, 78. The head piece 70 additionally includes lower strap means 80, 82 which extend through the depending strap loops 76, 78. The strap means 80, 82 have strap tabs 84, 86 at the ends thereof. The arrangement is such that the strap tabs 84, 86 may be secured at selected locations along the length of the associated one of the lower strap means 80, 82 to form lower connecting loops 88, 90. In this manner, the length of the lower connecting loops 88, 90 and hence the lower strap means 80, 82 may be individually adjusted to suit requirements.

To connect the head gear 68 to the mask 26, the second strap means 82 is threaded through the elongated opening 45 (FIGS. 2, 3) of the second connector 44 and then is bent back upon itself to form the lower connecting loop 90 shown in dotted outline in FIG. 8.

The lower connecting loop 88 of the lower strap means 80 is introduced through the entrance opening 20 (FIGS. 9 and 10A) so that the lower strap means 80 resides within the U-shaped slot 16 of the first connector means 10. Thereafter, each of the lower strap means 80, 82 is gradually tightened until a comfortable fit exists. Once the mask 26 is connected to a gas source, the lower strap tabs 84, 86 are unhooked and the lower strap means 80, 82 are again gradually tightened until an adequate seal and a comfortable fit exists.

Figure 10B:
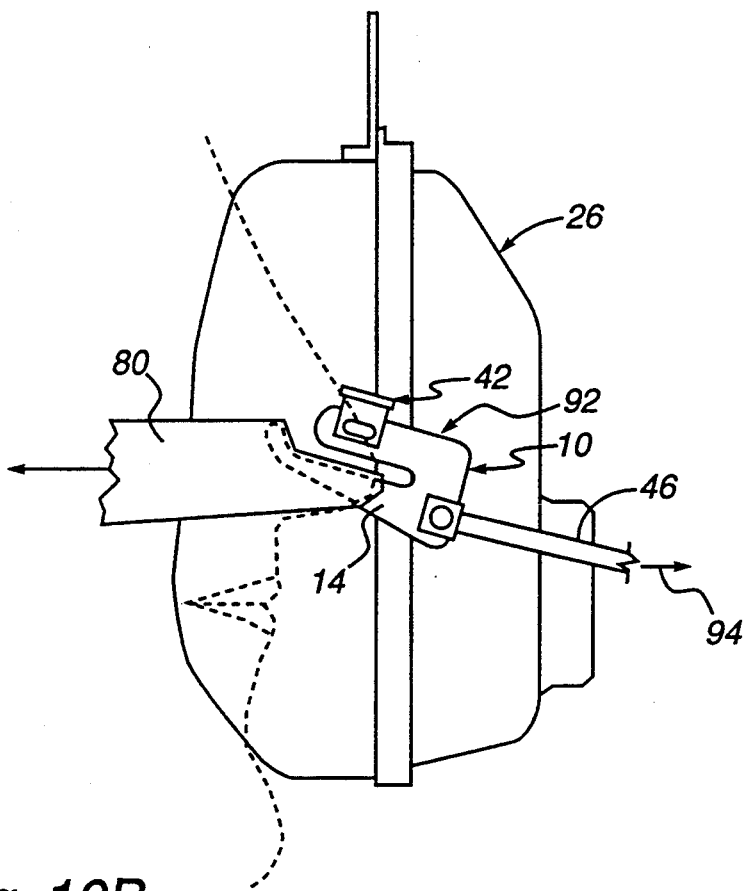
FIG. 10B is a side view similar to FIG. 4, illustrating inclination of the first connector means and the disengagement of the first strap means.

It will now become apparent that when it becomes necessary to remove the mask, the first connector means 10, the cord 46 and the pivot means 42 cooperate to allow for quick and easy removal of the mask 26. To this end, the pivot means 42 (FIG. 10A) supports the first connector means 10 in the upright position 62. The pivot means 42 allows resisted pivotal movement of the first connector means 10 from the upright position 26 to a second or inclined position 92, illustrated in FIG. 10B. The lower strap means 80 slides off of the arm 14 and is quickly disconnected from the first connector means 10. The mask 26 is thus released. It will be observed by comparing FIGS. 10A and 10B that as the cord 46 is pulled away from the mask 26 in the direction of the arrow 94, the first connector means 10 is pivoted about the pivot means 42 into the second or inclined position 92.

Once the lower strap means 80 has been disconnected from the first connector means 10 and upon release of the cord 46, the first connector means 10 returns to the upright position shown in FIG. 2. That is, the resilient material of the pivot means 42 causes the connector means 10 to assume the upright position 62. Therefore, when it is desired to reattach the mask 26 to the patient, the lower strap means 80 is again hooked over the arm 14 of connector means 10 as illustrated in FIG. 10A. As a result, the mask 26 is reattached to the patient without having to readjust for proper fit.

We claim:

1. A patient gas delivery system, comprising:
   mask adapted to fit over the face of a patient and having a first side and, opposite thereto, a second side;
   headgear adapted to fit over the head of a patient and including straps, one of said straps extending from each side of said headgear toward said mask;
   a first connector on said first side of said mask, presenting a generally vertical, U-shaped slot having an open top;
   a first of said straps being received in said U-shaped slot through said open top and detachably connecting said first of said straps to said first connector; and
   pivot means connecting said first connector to said first side of said mask for resisted pivotal movement of said first connector from an upright position wherein said first of said straps is connected to said first connector, to an inclined position wherein said first of said straps is quickly disconnected from said first connector and said mask is released from contact with the patient's face without need for removing said headgear from the patient's head; and means for pivoting said first connector from said upright position to said inclined position.

2. The patient gas delivery system as defined in claim 1 wherein said means for pivoting said first connector comprises:
   a cord having one end connected to said first connector and depending therefrom.

3. A patient gas delivery system as defined in claim 1 including
   a second connector on said second side of said mask, a second of said straps being connected to said second connector.

4. A patient gas delivery system as defined in claim 3 wherein said for pivoting said first connector means comprises:
   a cord having one end connected to said first connector and an opposite end connected to said second connector.

5. The patient gas delivery system as defined in claim 1 wherein said mask comprises an oral gas delivery mask.

6. The patient gas delivery system as defined in claim 1 wherein said mask comprises a nasal gas delivery mask.

7. The patient gas delivery system as defined in claim 1 wherein said mask comprises an oral/nasal gas delivery mask.

8. A gas delivery mask connectable to associated headgear having straps, said mask comprising:
   a shell adapted to receive conduit means for delivering gas to said mask, and connected thereto a relatively soft cushion having an opening adapted to receive the nose and/or mouth of a patient, said shell and cushion, in combination, presenting a first side and, opposite thereto, a second side of said mask;
   a first connector tab having a generally vertical U-shaped slot with an open top;
   pivot means connecting said first connector tab to said first side of said mask for resisted pivotal movement from a first position wherein said first connector tab is positioned for connection to straps of associated headgear to a second position wherein said first connector tab and hence said U-shaped slot thereof are inclined such that straps of associated headgear are quickly disconnectable from said first connector tab and said mask is released from engagement with the patient's face without first removing associated headgear from the patient's head; and means connected to said first connector tab for pivoting said first connector tab into said second position.

9. The gas delivery mask of claim 8 wherein said pivot means and said means for pivoting are connected to said tab on opposite sides of said U-shaped slot.

10. The gas delivery mask of claim 9 wherein said means for pivoting said tab resides below said U-shaped slot.

11. The patient gas delivery system as defined in claim 8 wherein said mask comprises an oral gas delivery mask.

12. The patient gas delivery system as defined in claim 8 wherein said mask comprises a nasal gas delivery mask.

13. The patient gas delivery system as defined in claim 8 wherein said mask comprises an oral/nasal gas delivery mask.

* * * * *